(12) United States Patent
Kupfer

(10) Patent No.: US 6,793,380 B2
(45) Date of Patent: Sep. 21, 2004

(54) ADJUSTABLE PROGRESSIVE JOINT-BRAKE SYSTEM

(75) Inventor: Stefan Kupfer, Fulda (DE)

(73) Assignees: Steris Inc., Temecula, CA (US); Ondal Industrietechnik GmbH, Hunfeld (DE)

( * ) Notice: Subject to any disclaimer, the term of this patent is extended or adjusted under 35 U.S.C. 154(b) by 0 days.

(21) Appl. No.: 10/373,902

(22) Filed: Feb. 25, 2003

(65) Prior Publication Data

US 2003/0161159 A1 Aug. 28, 2003

Related U.S. Application Data

(60) Provisional application No. 60/359,519, filed on Feb. 25, 2002.

(51) Int. Cl.[7] .............................................. F21V 21/00
(52) U.S. Cl. ...................... 362/371; 362/402; 362/288; 362/572; 362/804; 362/33; 403/117; 403/150; 248/325; 248/583
(58) Field of Search .................... 362/427, 33, 428, 362/41–419, 572; 403/117, 150; 248/325, 583

(56) References Cited

U.S. PATENT DOCUMENTS

| | | |
|---|---|---|
| 1,644,231 A | 10/1927 | Bosworth |
| 1,708,047 A | 4/1929 | Bosworth |
| 2,170,201 A | 8/1939 | Knapp .......................... 248/122 |
| 2,458,967 A | 1/1949 | Wiedenhoeft |
| 3,030,128 A | 4/1962 | Versen |
| 4,107,769 A | 8/1978 | Saluja |
| 4,418,798 A * | 12/1983 | Johannesen et al. ...... 188/73.45 |
| 4,494,177 A | 1/1985 | Matthews .................... 362/402 |
| 4,545,555 A | 10/1985 | Koch |
| 4,553,649 A * | 11/1985 | Bailey et al. ................ 188/340 |
| 4,770,384 A | 9/1988 | Kuwazima et al. ....... 248/281.1 |
| 6,012,821 A | 1/2000 | Yeaney et al. ................. 362/33 |
| 6,328,458 B1 * | 12/2001 | Bell et al. ..................... 362/371 |
| 6,471,363 B1 * | 10/2002 | Howell et al. ................. 362/11 |

FOREIGN PATENT DOCUMENTS

EP          392303 A1     10/1990

* cited by examiner

Primary Examiner—Alan Cariaso
Assistant Examiner—Ali Alavi
(74) Attorney, Agent, or Firm—Fay, Sharpe, Fagan, Minnich & McKee, LLP

(57) ABSTRACT

A joint (52) for connecting arm portions (40, 42) of a ceiling or wall mounted support system includes housing members (60,62) with an annular bearing (64) interposed between opposed surfaces (82,84) thereof. The housing members are clamped together on an axle (98) such that a braking force generated between the bearing and the housing member surfaces opposes rotation of one arm portion relative to the other. A variable braking force is generated between the bearing and surfaces (206) of the housing members which are generally perpendicular to the opposed surfaces (82,84). The variable braking force is generated by a spring (182) and is greatest when the arm supporting a piece of equipment (24, 26, 28, 56) is at its lowest point, relative to the horizontal. This overcomes the increased forces in the spring which otherwise tend to cause the arm portion (42) to drift upward.

22 Claims, 10 Drawing Sheets

ADJUSTABLE PROGRESSIVE JOINT-BRAKE SYSTEM

This application claims the priority of U.S. Provisional Application Ser. No. 60/359,519, filed Feb. 25, 2002.

BACKGROUND OF THE INVENTION

The present invention relates to the field of light supports. It finds particular application in conjunction with an adjustable lighting assembly for use in operating theaters, dental surgeries, and the like, and will be described with particular reference thereto. It should be appreciated, however, that the invention is also applicable to a wide variety of supported lighting applications.

Jointed supports are commonly used for positioning surgical lights in hospital operating rooms, dental surgeries, and the like to illuminate surgical sites on patients. The support is used to suspend one or more lightheads from a ceiling or wall mount and allows the lighthead to be moved in plural degrees of freedom within the operating room to various positions. It is desirable for the arm of the support to counterbalance the associated lighthead when the lighthead is in any position within a range of positions. A spring is typically carried by the arm to assist in balancing the arm. However, the arm often tends to drift over time, and the light head moves out of position. Additionally, the spring is not able to fully compensate for differences in the forces which occur when the arm is positioned in different angular orientations.

The present invention provides a new and improved adjustable progressive joint brake system and method of use, which overcome the above-referenced problems and others.

SUMMARY OF THE INVENTION

In accordance with one aspect of the present invention, a system for movably positioning a piece of equipment relative to an examination site is provided. The system includes a first arm portion and a second arm portion directly or indirectly connected with the piece of equipment. A joint interconnects the first arm portion and the second arm portion. The joint includes a first housing member connected with the first arm portion and a second housing member connected with the second arm portion. A bearing is interposed between the first and second housing members. A clamping assembly clamps the first and second housing members on the bearing with sufficient force to provide a linear brake force on the bearing. A spring arm mechanism applies a radial brake force on the bearing which varies according to the position of the second arm portion.

In accordance with another embodiment of the present invention, an arm assembly is provided. The arm assembly includes first and second arm portions and a joint for positioning the second arm portion in a range of rotational orientations relative to the first arm portion. The joint includes a bearing and first and second opposed housing members which apply a first braking force to the bearing. A spring arm mechanism is connected with the joint and is at least partially received in the second arm portion. The spring arm applies a second braking force to the bearing in a direction generally at right angles to the clamping force. The second bearing force is variable, dependent on the rotational orientation of the second arm portion relative to the first arm portion.

In accordance with another embodiment of the present invention, a method of balancing an arm portion of an arm assembly is provided. The arm assembly includes a joint having first and second relatively rotatable housing members spaced by a bearing. The arm portion is connected to the second housing member. The method includes applying a clamping pressure between the housing members and the bearing in a first direction to create a constant braking force which resists rotation of the second housing member relative to the first housing member. The method further includes applying a variable clamping pressure between at least one of the housing members and the bearing in a direction generally perpendicular to the first direction to provide a variable braking force which resists rotation of the second housing member relative to the first housing member, the variable clamping pressure varying according to the relative rotational positions of the first and second housing members.

One advantage of at least one embodiment of the present invention is that it enables a spring arm to remain in place in a defined position, even when the center of gravity of a light to which it is attached moves.

Another advantage of at least one embodiment of the present invention is that it enables a brake system to be adjusted to generate a varying brake force.

Another advantage of at least one embodiment of the present invention is that a spring arm is optimally adjusted by a combination of spring tension and brake action, allowing the spring arm to be set to any position within a range of angular positions.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
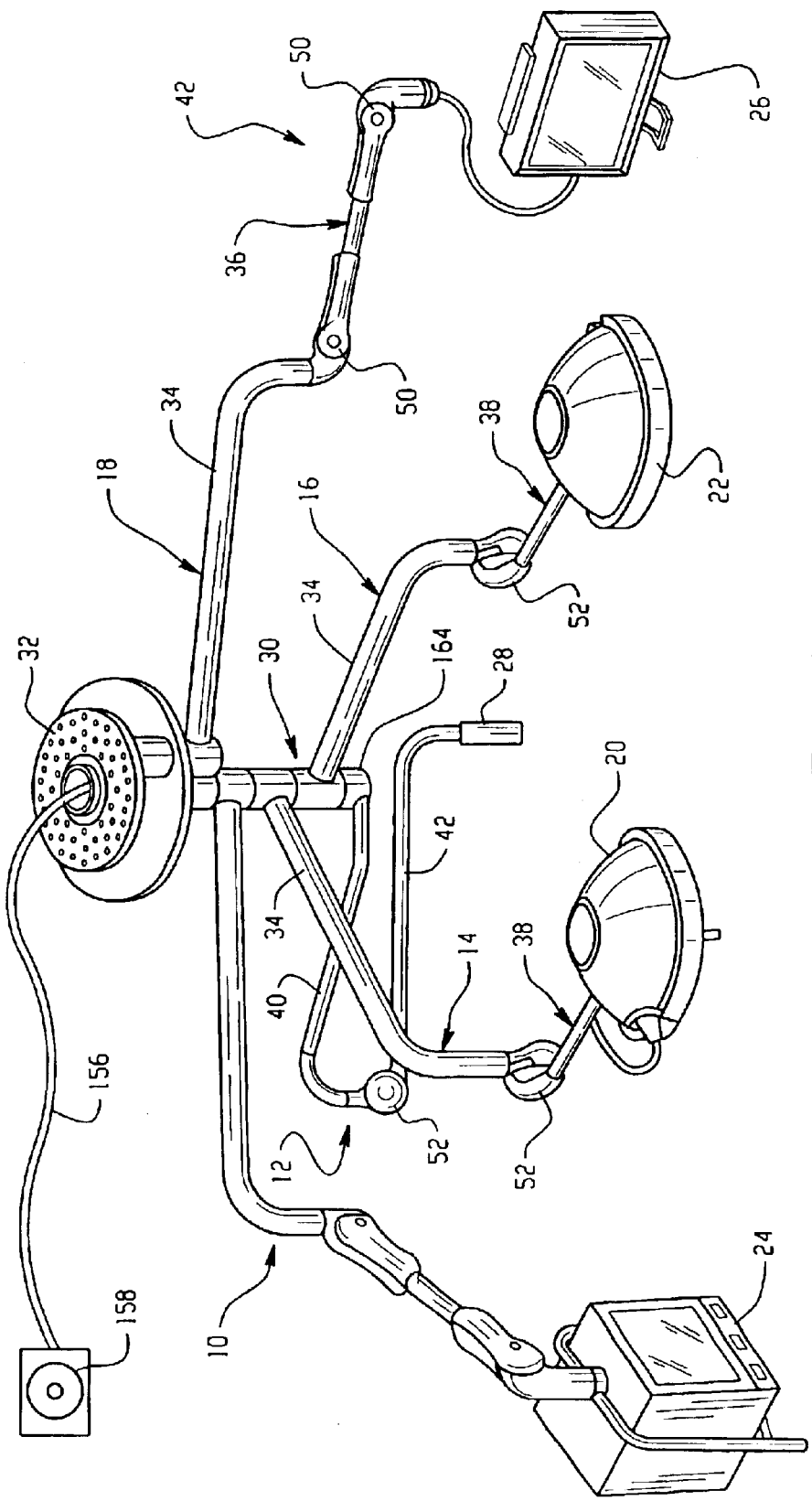
FIG. 1 is a perspective view of a lighting system according to the present invention.

With reference to FIG. 1, a lighting system includes several pivoting arm assemblies for supporting lights and other equipment above a patient or other site to be illuminated or examined. Specifically, the lighting system includes a first arm assembly 10, a second arm assembly 12, a third arm assembly 14, a fourth arm assembly 16, and a fifth arm assembly 18, each one configured for supporting a lighthead 20, 22, monitor 24, 26, a flexible task light 28, or other piece of equipment to be used during a dental or surgical procedure. While the lighting system is described with particular reference to a surgical lighting system, as illustrated in FIG. 1, it is appreciated that the system may comprise a single pivoting arm assembly or several assemblies for a variety of different applications.

The arm assemblies 10, 12, 14, 16, 18 are mounted by a central hub 30 to a support member 32, such as a ceiling or wall-mounted plate. The arm assemblies 12, 14, 16 allow each of the lightheads 20, 22, and a light emitting component (not shown) of the task light 28 to be positioned for achieving a desired level of illumination on a subject under examination. The arm assemblies are articulated to allow the equipment to be positioned. Specifically, the arm assemblies each include two or more arm portions 34, 36, 38, 40, 42, 44 which are articulated about joints 50, 52. Each arm assembly may have more than one joint, depending on the number of arm portions.

With reference now to FIGS. 2–9, at least one of the joints 52 employs a joint brake system, described in more detail below, which allows a spring arm 42 to which it is attached to remain in place in a defined position even if the center of gravity of the flexible task light 28 (FIG. 1), lighthead 56 (FIG. 9), or other equipment to which it is attached moves. It will be appreciated that the same joint and brake system are advantageously employed for all the joints, although it is also contemplated that some of the joints 50 in the lighting system operate in a conventional fashion.

Figure 4:
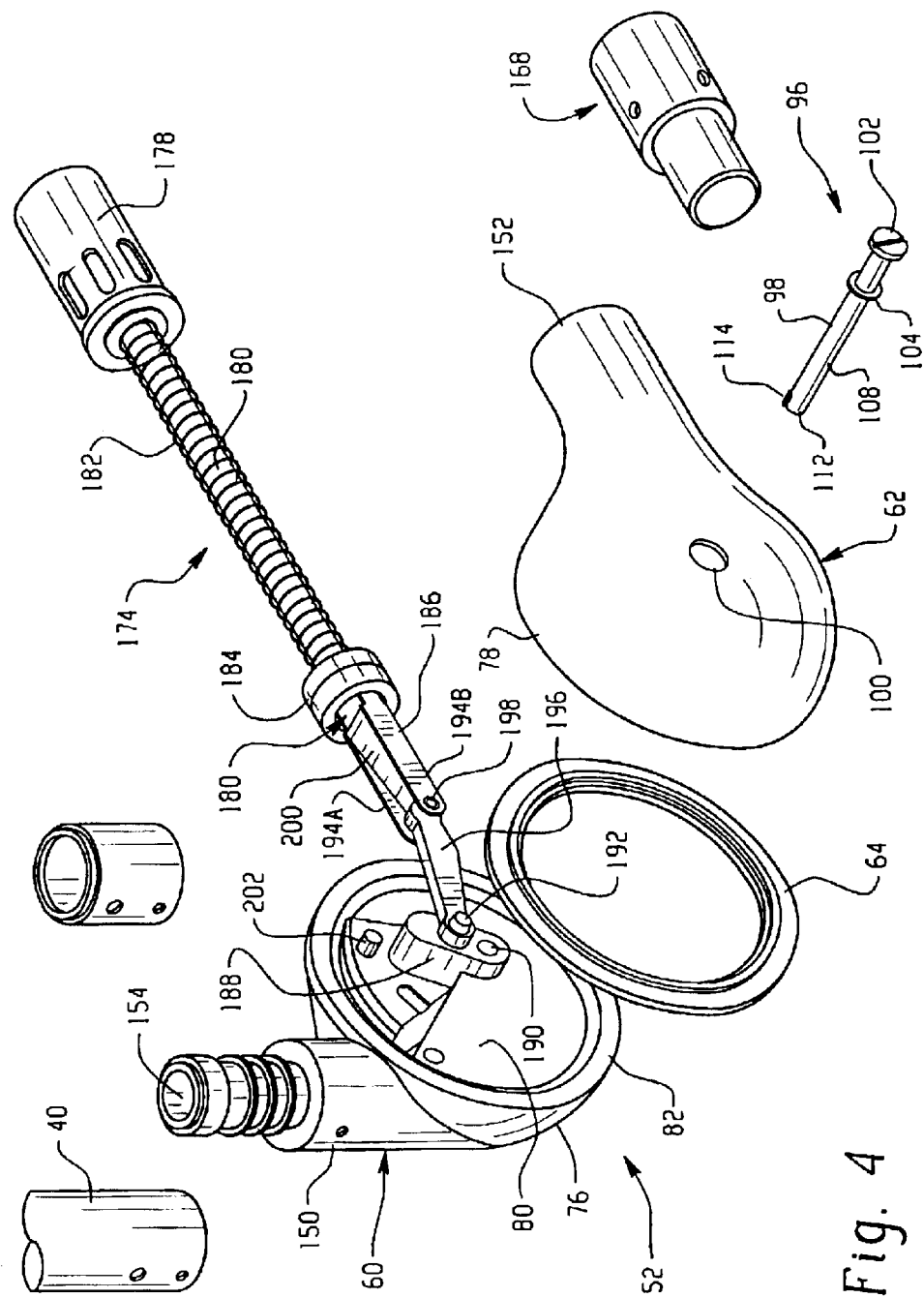
FIG. 4 is an exploded perspective view of the joint of the arm assembly of FIG. 2.
Figure 5:
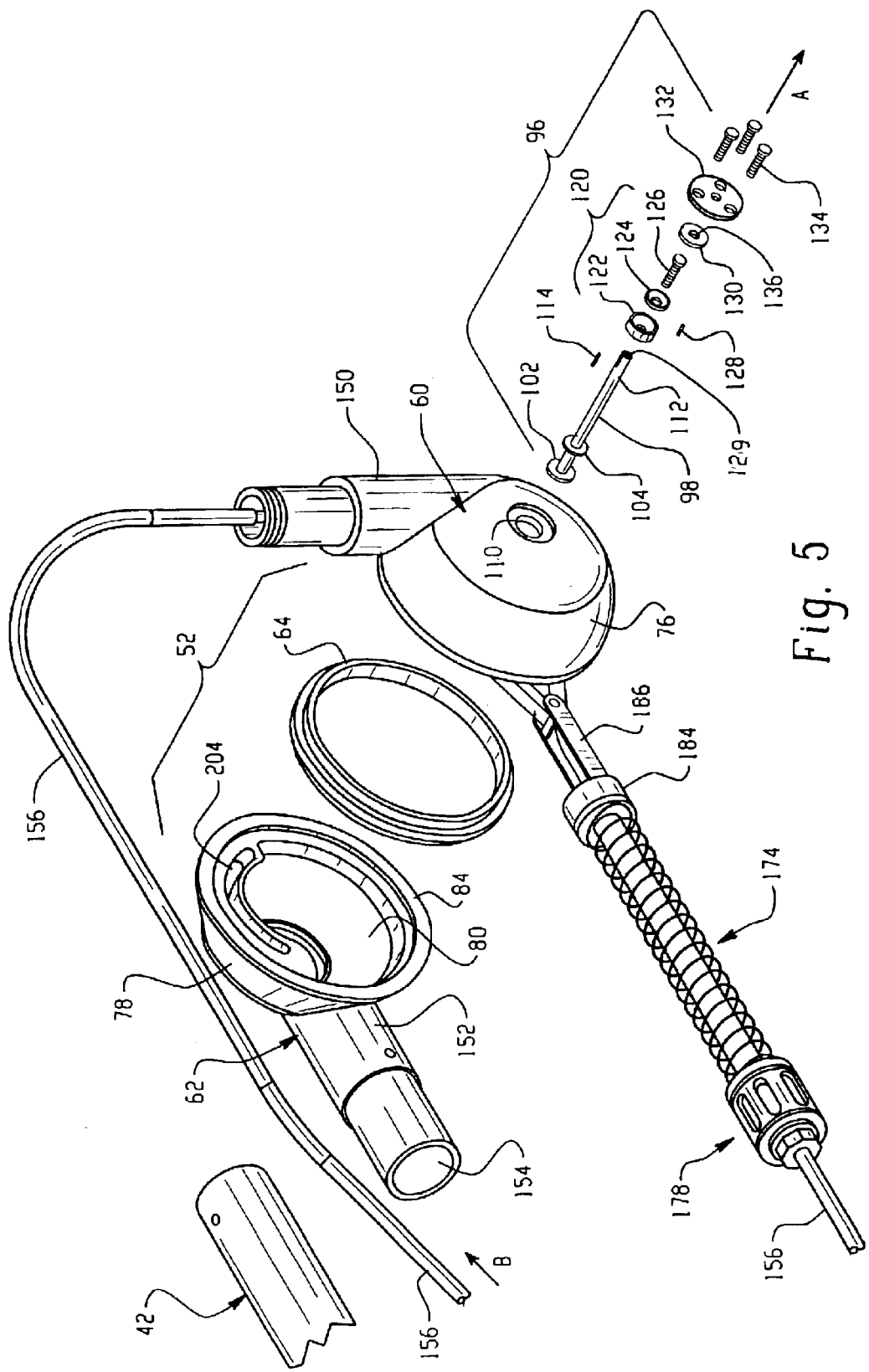
FIG. 5 is another exploded perspective view of the joint of the arm assembly of FIG. 2.

As shown in FIGS. 4 and 5, the joint or joints 52 employing the joint brake system includes a pair of opposed housing members 60, 62 with an annular bearing 64 disposed between the housing members. The bearing is formed from a polymeric material, such as a polyamide, or other suitable material, which permits sliding of the adjacent housing member surfaces on the bearing. The housing members 60, 62 thus move relative to each other via the sliding characteristics of the bearing 64.

Figure 8:
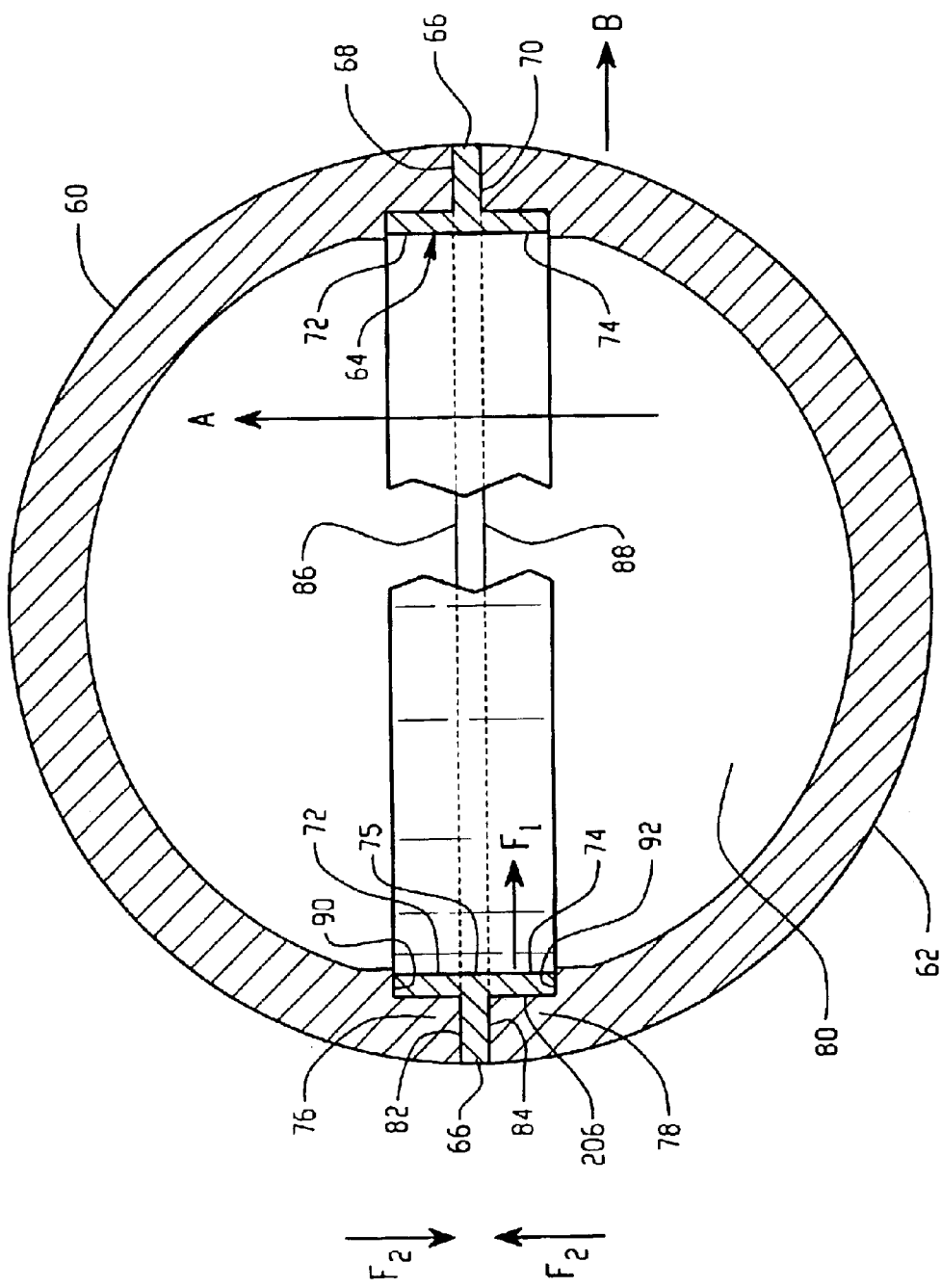
FIG. 8 is a schematic cross-sectional view showing forces on the bearing ring of the joint of FIG. 2.

The bearing 64 is particularly adapted to carry both axial and radial forces. Specifically, as shown in FIG. 8, the bearing 64 includes an annular disk portion 66 with opposed surfaces 68, 70. Radial flanges 72, 74 extend generally perpendicular to, and in opposite directions from the surfaces 68, 70 of the disk 66 at an inner peripheral edge 75 of the disk, giving the bearing 64 an overall T-shaped cross section. The housing members 60, 62 each include a cup portion 76, 78, respectively, each cup portion having a hollow interior 80 and an annular bearing surface 82, 84 at an open end 86, 88 thereof. The disk portion 66 of the bearing 64 is seated between the opposed annular surfaces 82, 84 with each of the radial flanges 72, 74 being received on a step or shelf 90, 92, adjacent the respective open end 86, 88. The friction created by the bearing 64 provides for braking, as will be described in greater detail below.

Figure 6:
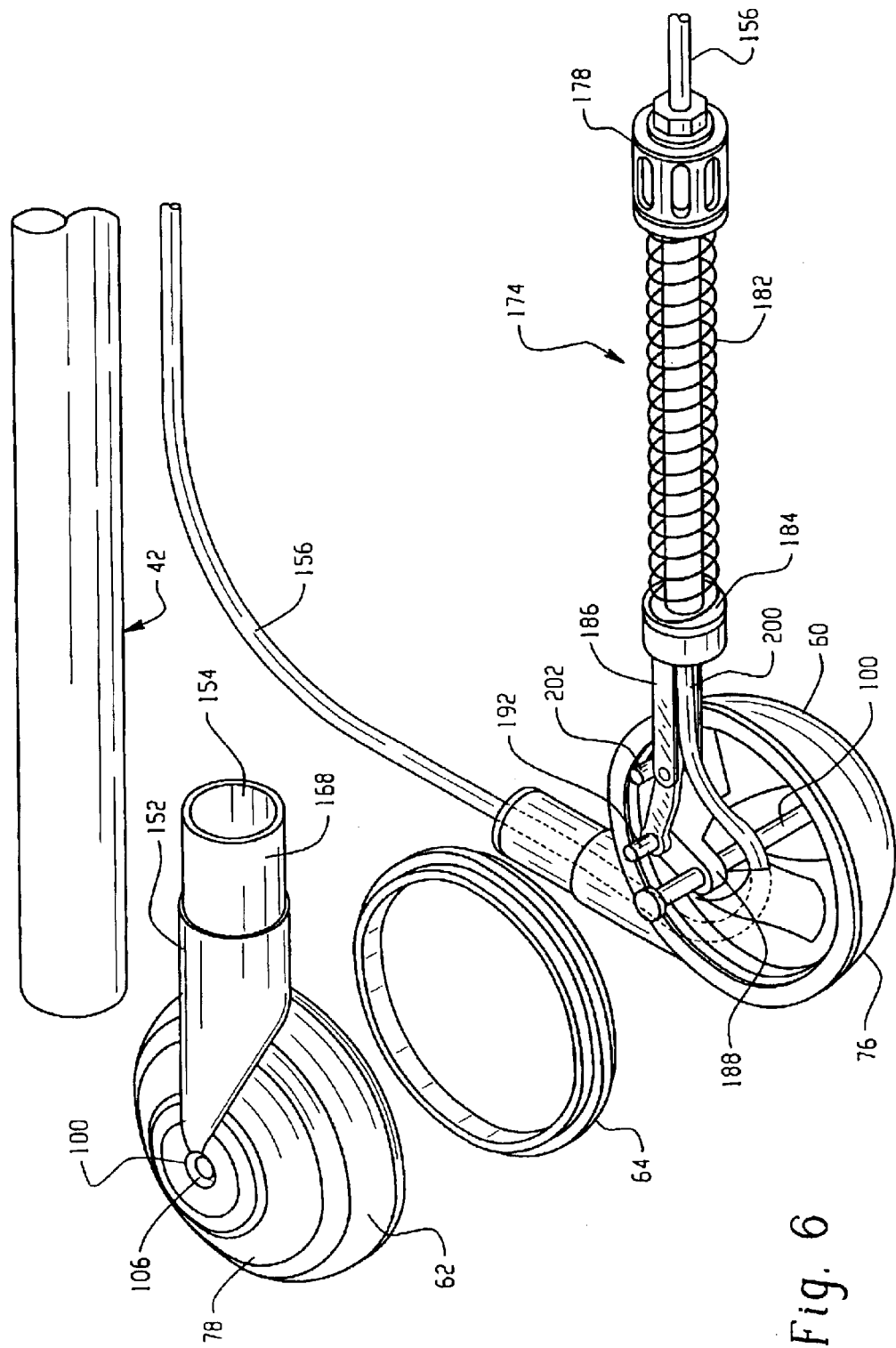
FIG. 6 is another exploded perspective view of the joint of the arm assembly of FIG. 2.

With particular reference to FIGS. 4–6, the housing members 60, 62 are clamped together by a clamping assembly 96. Specifically, the housing members 60, 62 are releasably connected by a transverse axle or pivot pin 98 extending therebetween. The axle 98 is received through a central hole 100 in the cup portion 78 of housing member 62. A head 102 of the axle is seated on a washer 104 in a recess 106 around the hole 100. A shaft 108 of the axle passes through the hole 100 and through a corresponding central hole 110 in the cup portion 76 of housing member 60. A distal end 112 of the axle shaft 108 is secured to the housing member 76 with a feather key 114. The feather key prevents relative rotation between the housing member 60 and the axle shaft 108.

Figure 7:
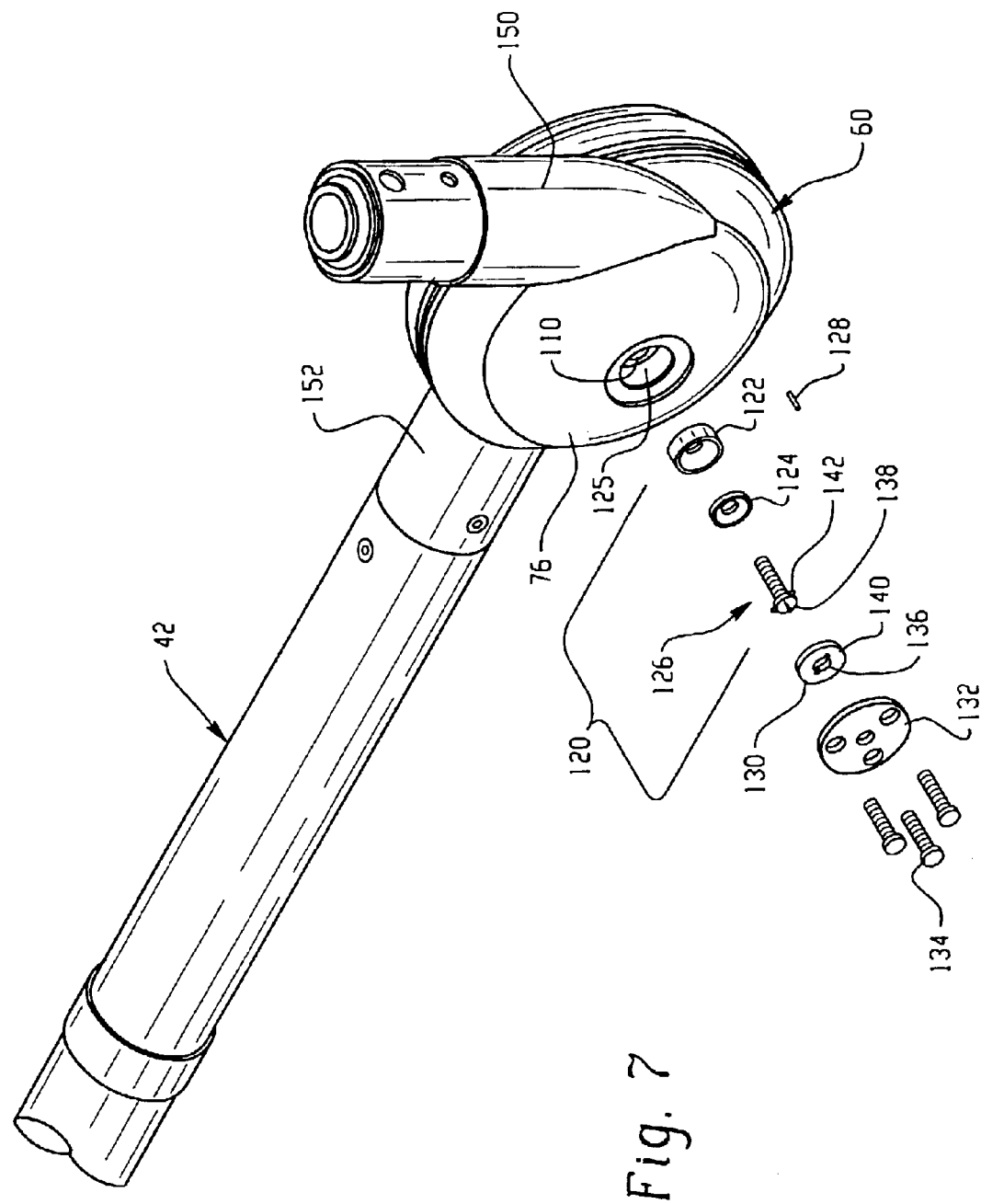
FIG. 7 is another, partially exploded perspective view of the joint of the arm assembly of FIG. 2.

As shown in FIGS. 5 and 7, the housing members 60, 62 are clamped together on the axle 98 by a clamping means 120 of clamping assembly 96. The illustrated clamping means 120 includes a clamping assembly holder 122, a screw support 124 and a means for variably adjusting the clamping pressure, such as a brake screw 126. The holder 122 and screw support 124 are received in a recess 125 around the hole 110 and are locked to the housing member 60 by a pin 128. The brake screw 126 has a threaded shaft which is received within a correspondingly threaded bore 129 at the distal end of the axle 98. The brake screw shaft passes first through central apertures in the clamping assembly holder 122 and in the screw support 124. Clockwise rotation of the brake screw 126 draws the axle shaft in the direction of arrow A (FIG. 5), bringing the housing members 60, 62 into clamping relationship on the bearing 64.

The brake screw 126 is adjusted (i.e., threaded or unthreaded) until the housing members 60, 62 are clamped under a desired degree of tension, as will be described in greater detail below, in which the housing members can be rotated, relative to one another, when a sufficient rotational force is applied. The clamping of the housing members on the bearing provides a linear braking force which is adjustable by means of the brake screw. Once the adjustment has been made, the brake screw 126 is held in position relative to the housing member 60 by a brake disk 130, which is clamped by a cap 132 and screws 134 onto the holder 122 and housing member 60. As best shown in FIG. 7, the brake disk 130 has a central opening 136 which is of sufficient diameter to receive a head 138 of the brake screw 126. Two keyhole slots 140 extend radially from opposite sides of the opening and are adapted to receive corresponding lateral protrusions 142 formed on the brake screw head (for example, by a pin which passes through the head). The slots 140 prevent the brake screw from rotating relative to the disk 130 which is held fixed to the housing member 60 as noted above. The disk 130 thus maintains the position of the brake screw, preventing unintended rotation of the screw during operation of the joint.

While the axle 98 is shown as being clamped to the housing member 60, it is also contemplated that the axle could alternately be clamped to the second housing member 62, with the first housing member being rotatable about the axle. For example, the axle could pass through the housing members in an opposite direction to that shown in FIGS. 4 and 5, with the clamping mechanism attached to housing member 62.

As shown in FIG. 4, the housing members 60, 62 each include a hollow tube portion 150, 152. The tube portions 150, 152 extend from the cup portions 76, 78, respectively, and proximal ends of interior bores 154 thereof access the hollow interiors 80 of the cup portions. The tube portions 150, 152 are threaded, bolted, welded or otherwise connected at distal ends thereof to respective hollow arm portions 40, 42. In one embodiment, the tube portion 150 is releasably connected to the arm portion 40, allowing the joint 52 and spring arm 42 to be replaced with different joint and spring arm assemblies as desired. For example, the task light 28 may thus be interchangeable with a lighthead 20, 22.

As shown in FIGS. 5 and 6, the tube portions 150, 152 serve as inlet and outlet, respectively, to the joint 52 for a cable sheath 156. In a preferred embodiment, the cable sheath 156 carries within it a fiberoptic cable (not shown), which carries light from a light source 158 (FIG. 1) to the tip of the manual task light 28. The cable sheath 156 (or interconnecting portions thereof) thus extends from source 158, which may include an incandescent bulb, through the hub 30 and into arm portion 40 via a suitable hub connector, such as connector 164, which is pivotable relative to the hub 30. The sheath 156, and fiberoptic cable within it, is carried from the arm portion 40 to the spring arm 42 via the joint 52 and then to the distal tip of the flexible task light 28.

Figure 9:
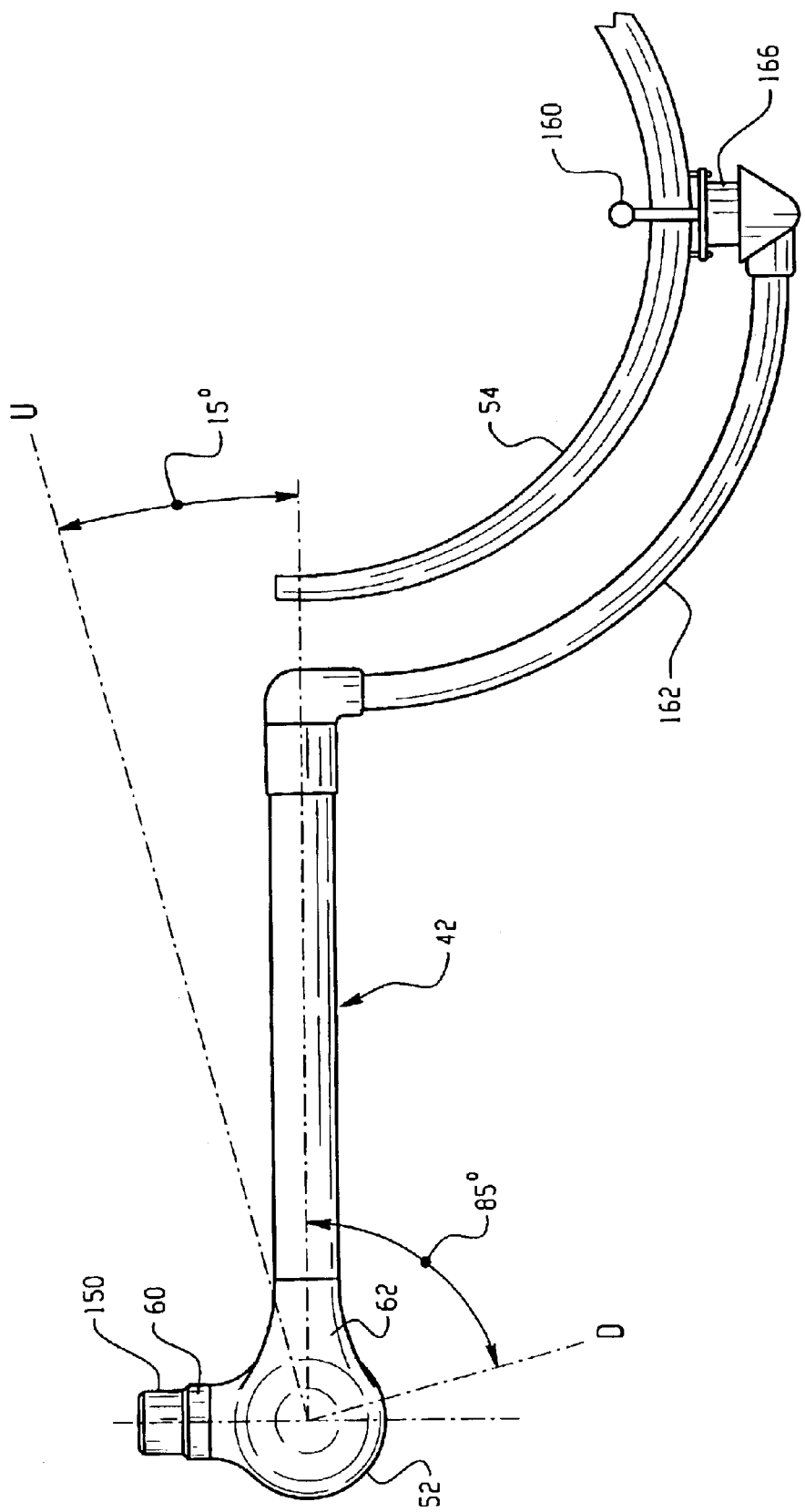
FIG. 9 is a schematic view showing the range of positions for the spring arm of FIG. 2.

Alternatively, as shown in FIG. 9, the cable sheath is carried through the spring arm 42 and the fiberoptic cable carries light to a light outlet 160 mounted within the lighthead 54. The lighthead is mounted to a distal end of the spring arm 42 by a yoke 162. The cable sheath 156 optionally passes through the yoke to a connector 166, which provides a releasable interconnection between the lighthead and the yoke 162.

Alternatively, or additionally, the cable sheath 156 carries electrical wiring for supplying current to a conventional bulb mounted in a lighthead or to operational elements of the lighthead, such as lens focussing systems, and the like. When the spring arm 42 is connected to a monitor, such as monitor 24, the cable sheath carries audiovisual input and output connection cables. In yet another embodiment, the wiring and/or fiberoptic cable is carried separately from the arm assembly or are passed between arm portions outside the joint.

Figure 2:
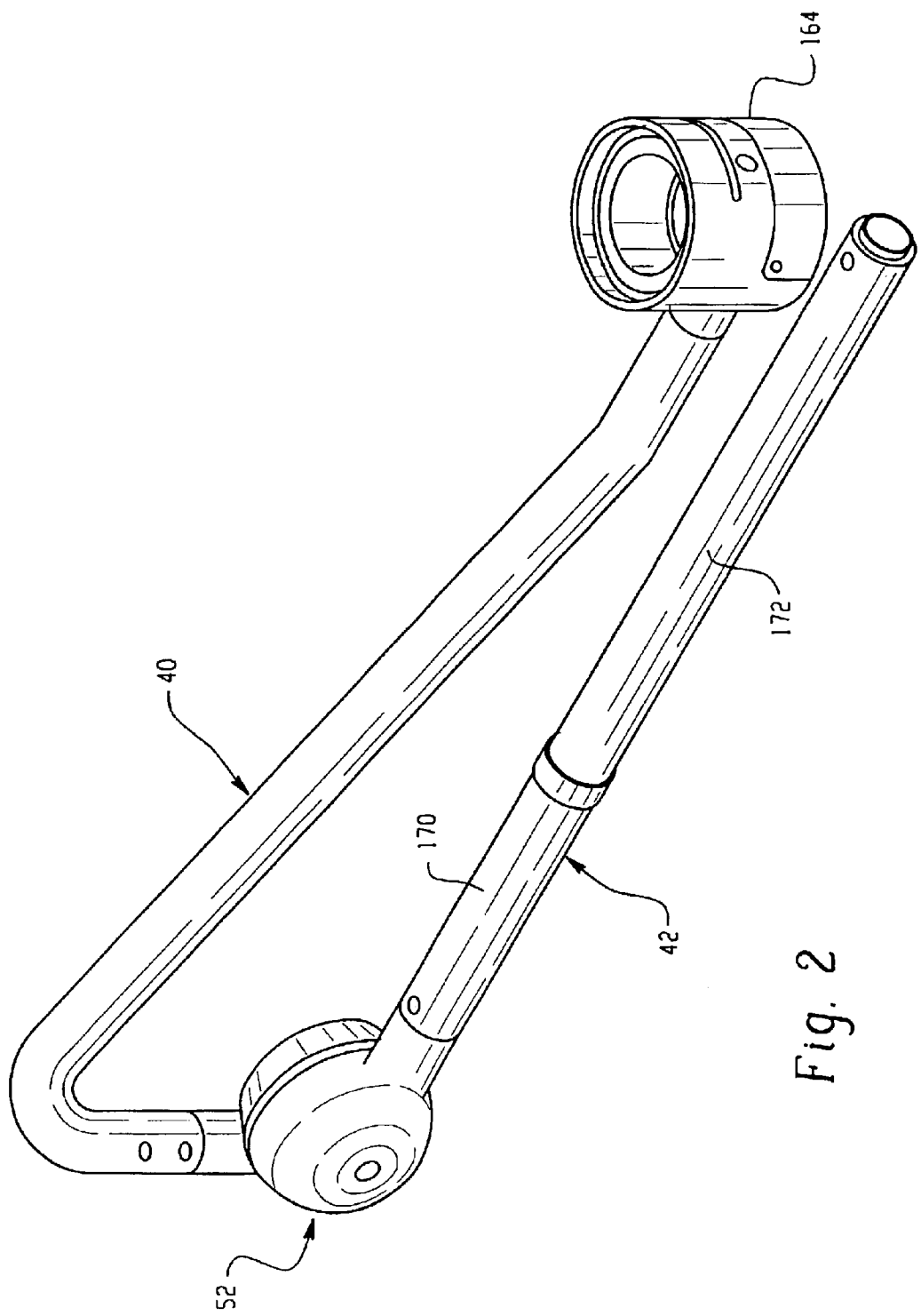
FIG. 2 is an enlarged perspective view of a jointed arm assembly of the lighting system of FIG. 1.
Figure 3:
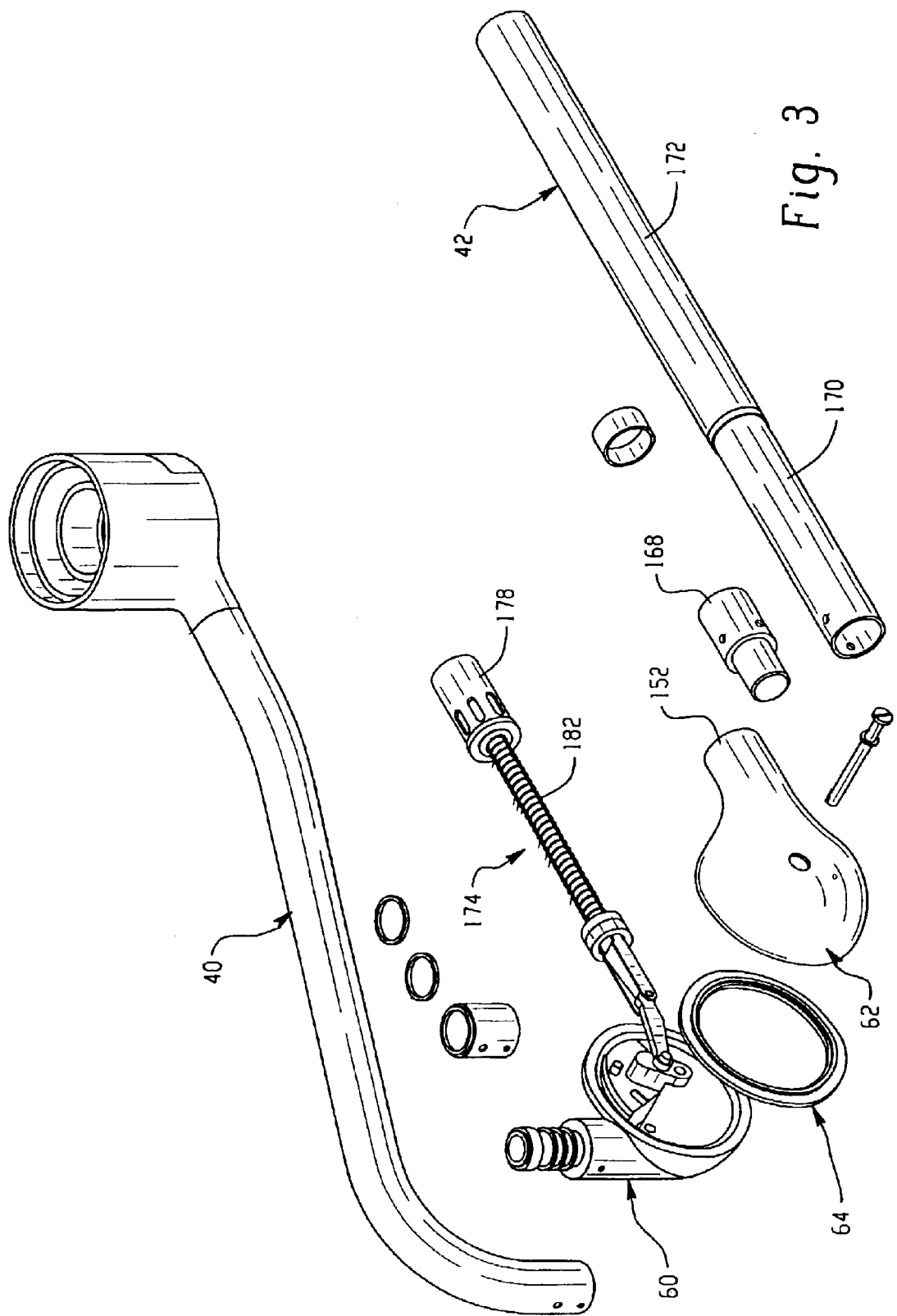
FIG. 3 is an exploded perspective view of the arm assembly of FIG. 2.

As shown in FIGS. 2 and 3, the spring arm 42 includes an adaptor 168 and first and second tubular sleeve portions 170, 172. The sleeve portions are slidingly connected together. The sleeve portion 170 is rigidly attached to tube portion 152 of housing member 62 via the intermediate adaptor 168. The sleeve portion 170 receives both the cable sheath 156 and a spring arm mechanism 174 therethrough. The second sleeve portion 172 is telescopingly received in an end of the first sleeve portion 170 to create an extensible arm 42.

As shown in FIG. 4, the spring arm mechanism 174 includes an internally threaded adjustment nut 178, which is mounted to one end of a correspondingly externally threaded hollow rod 180. The rod defines an inner bore adapted to carry the cable sheath 156 therethrough. A force application means, such as a coil spring 182 is supported around the rod 180 and extends between the adjustment nut and a force transferring member 184, which is advantageously shaped as a disk. The disk 184 is received around the other end of the rod 182. The disk 184 is seated on an interior shelf (not shown) within the adaptor 168, which limits axial movement of the disk in the direction of the joint. The spring is held under compression between the adjustment nut 178 and the disk 184, which pushes the disk up against the interior shelf in the direction of arrow B (FIG. 5). By rotating the adjustment nut 178 in one direction, the effective length of the rod 180 increases, thereby decreasing the compression in the spring 182 accordingly. By rotating the adjustment nut 178 in an opposite direction, the effective rod length decreases, thereby increasing the compression in the spring accordingly. The spring 182 tends to overcome this compression by drawing on a linkage 186 and pushing the disk 184 harder against the interior shelf. Preferably, the tube 172 includes a window (not shown) providing access to the adjustment nut, allowing adjustments to be made using a straight rod, or the like.

The rod 180 is pivotally mounted by the pivotable linkage 186 to a block 188 (FIG. 6). The block is rigidly mounted to the housing member 60, within the interior space 80. A bore 190 within the block 188 (FIG. 4) receives the axle 98 therethrough. Specifically, the pivotable linkage 186 is connected to the block by a pivot pin or bolt 192 at a point which is radially spaced from the axle, such that rotation of the housing member 62 and spring arm 42 in one direction (clockwise) increases a compression force on the spring 182, while rotation in the opposite direction (anticlockwise) decreases the compression force in the spring.

As best shown in FIG. 4, the pivotable linkage includes a first linkage portion 194 comprising a pair of parallel, spaced arms. The arms 194A, 194B are connected adjacent one end of the rod 180 and at the other end to a second linkage portion 196 by a pivot pin 198. Pivoting of the two portions 194, 196 allows the bolt 192 to move away from the axis of the rod 180 as the block 188 rotates around the axle 98.

The spring arm mechanism 174 extends within sleeve portion 170 and shoulder portion 168 and is guided into the tube portion 152 of housing member 62. The fiber optic cable sheath 154 is lead through the joint 52 by first inserting it into and then feeding it through the spring arm mechanism 174. A cable guide 200, located between arms of linkage 186, is provided to ensure that the cable 18 is automatically routed through the spring arm mechanism 174 and along the cable guide to tube portion 150 of housing member 60.

Figure 11:
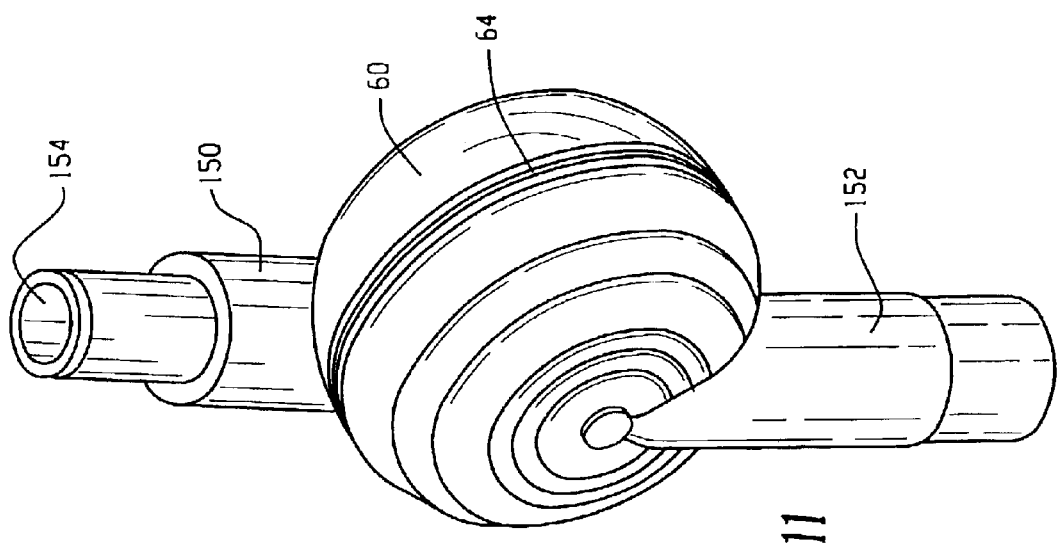
FIG. 11 is a perspective view of the joint of FIG. 2 in a lower position.
Figure 10:
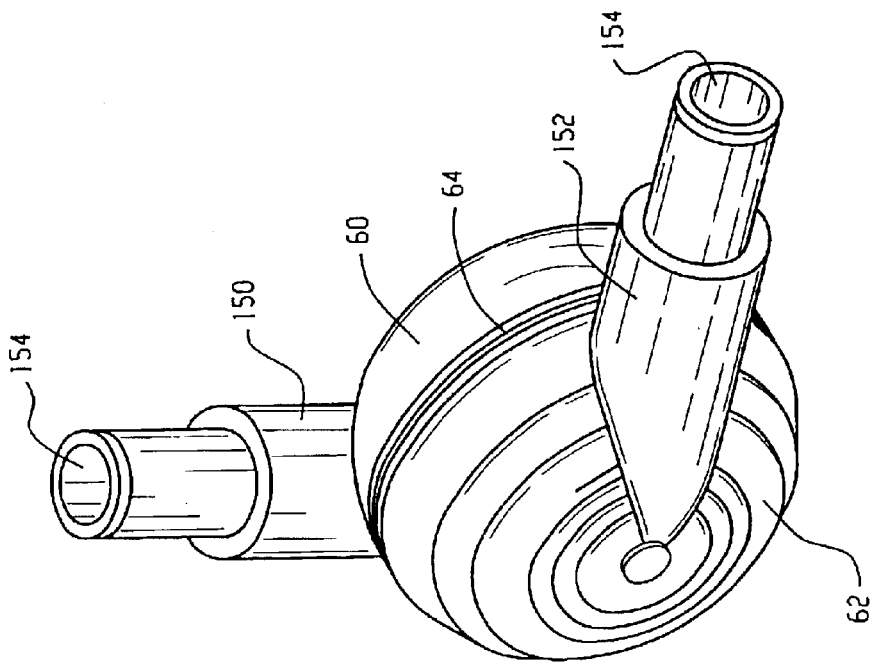
FIG. 10 is a perspective view of the joint of FIG. 2 in an upper position.

As shown in FIGS. 4, 5, and 6, a pin 202 extends from the block 188 at a point radially spaced from the bore 190 and the bolt 192. The pin slides along a curved slot 204 (FIG. 5) formed in the cup portion 78 of housing member 62, adjacent the open end. The slot limits the amount of rotation of the housing member 60 with respect to housing member 62. In a preferred embodiment, the pin 202 and slot 204 permit a maximum of about 100° of relative housing member rotation. For example, as shown in FIGS. 9, 10, and 11, if the tubular portion 150 of housing member 60 is aligned in a vertical orientation, the housing member 62 is rotatable such that the spring arm 42 is positionable in a first orientation U (FIG. 10), which is approximately 15° above the horizontal and can be rotated through 100° to a second orientation D (FIG. 11), which is approximately 85° below the horizontal, i.e., almost colinear with the tube portion 150. The arm 42 can be selectively positioned at any radial position intermediate these two orientations U, D.

The compressive forces generated within the spring 182 vary based upon the angle of the spring arm 42 relative to the upper arm 40. When the spring arm is in position U (FIG. 10), the compression force in the spring, which acts on the rod 180 to draw it away from the joint 52, is at a minimum. As the spring arm 42 is rotated towards position D (FIG. 11), the spring force increases. This spring force acts to try to push the arm 42 upwards, toward position U. The increasing spring force also tends to pull the cup portion 78 of housing 62 relative to cup portion 76 of housing 60 in a direction B along the axis of the spring arm 42, as shown in FIGS. 5 and 8. Specifically, the disk 184 is pressed by the spring 180 more firmly against the interior shelf of adaptor 168 with sufficient force to push the adaptor and the entire housing member 62 a small distance in the direction indicated by arrow B (i.e., in a direction generally perpendicular to axle 98 and the force applied in the direction of arrow A by the clamping of the two housing members together). This creates radial forces $F_1$ between the cup portions 76, 78 and the radial flanges 72, 74. Depending on the relative angular position of housing member 62 to housing member 60, the radial force applied on bearing ring 64 by the spring arm 42 varies. A maximum radial force component on the bearing 64 is achieved with a maximum position of 85° below horizontal. As a result, a progressively increasing brake force component $F_1$ is generated as the spring arm moves from the minimum position U to the maximum position D. The force is generated between sidewalls 206 of the steps 90, 92 and the adjacent surfaces of the radial flanges 72, 74 of the bearing. This braking force tends to clamp the housing members more firmly together, thus resisting the tendency of the spring arm 42 to rise due to the increasing spring compression. The friction force essentially overcomes the force of the compressed spring to thereby hold the arm in place.

The hole 100 in housing member 62 is sufficiently large or is elongate in a direction parallel with arrow B that it allows the small amount of relative movement between the housing member 62 and the axle 98 and housing member 60 in the direction of arrow B.

Additionally, by clamping both housing members 60, 62 together with the brake screw 126, a linear braking force $F_2$ is produced on the disk portion 66 of the bearing ring 64 in the direction of arrow A, i.e. the linear braking power does not depend on a position of the spring arm 42, but depends only on the degree of tightening of brake screw 126. Thus, when the spring arm 42 is in its lowest position and the spring 182 is tending to rotate the arm back toward a horizontal position, the increased braking force $F_1$ generated between the bearing 64 and the housing members 60, 62 which acts in the direction of arrow B resists this tendency and the spring arm remains fixed in its lower position.

The joint 52 can be set for different load ranges by changing the tension of the spring 182 via the adjustment nut 178. Alternatively or additionally, the joint 52 is also set for different load ranges by changing the distance between the bolt 192 and the axle 98. Specifically, the bolt is moved closer to or further from the axle in a slot (not shown) formed in the block.

Referring to FIGS. 9 and 10, in the position U, 15° above horizontal, the spring arm 42 has the lowest spring generated clamping power which results in the lowest radial braking force. In the position of 85° (FIG. 11) below horizontal, the spring arm has the highest spring generated clamping power which generates the largest radial braking force. Between these two positions, a progressively varying braking force component is produced.

The adjustable progressive joint brake system thus allows the spring arm 42 to remain in position, without "drifting," when the center of gravity of the task light 28 or lighthead 56 moves. The spring arm 42 is balanced during assembly by adjusting the compression in the spring 182 and also by adjusting the braking mechanism. Thus, the spring arm is adjusted by a combination of spring tension and brake action, that is, the spring arm can be set to any position and remains in place.

If the center of gravity of the light moves, for example, by flexing the flexible task light 28 or tilting the light head 56 relative to yoke 162, balancing of the spring arm is performed by the spring and also by the linear braking mechanism. The linear braking mechanism is adjustable as necessary (for example, if the lighthead is replaced by one of a different size and weight) and generates a varying brake force, depending on the degree of adjustment of the brake screw. When the spring arm is used in a vertical swivel range of 100 (i.e., between about +15° above horizontal and about −85° below) the spring arm and the light move additionally. The arm remains stable even with a load torque of 0 N.m or a negative torque. Thus, the spring arm is optimally adjusted by a combination of spring tension and brake action (i.e., the spring arm can be set to any position and remain in place). When the joint remains stationary in the vertical plane, the static friction in the bearing brake system is also used to secure the position. Thus, the brake mechanism acts on the system to provide a linear braking force and as a progressively increasing radial braking force, depending on the position of the spring arm and the vertical plane.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for movably positioning a piece of equipment relative to an examination site, the system including:
   a first arm portion;
   a second arm portion directly or indirectly connected with the piece of equipment; and
   a joint which interconnects the first arm portion and the second arm portion, the joint including:
      a first housing member connected with the first arm portion,
      a second housing member connected with the second arm portion and rotatable relative to the first housing member,
      a bearing interposed between the first and second housing members, and
      a clamping assembly which clamps the first and second housing members on the bearing with sufficient force to provide a linear force on the bearing in a first direction; and
      a spring arm mechanism which applies a radial braking force on the bearing in a second direction, the radial braking force varying according to an angular position of the second arm portion.

2. The system of claim 1, wherein the piece of equipment includes a light emitting component.

3. The system of claim 2, further including:
   a fluorescent cable, the cable running through the first and second arms and the joint to provide the light emitting component with light from a remote light source.

4. The system of claim 1, wherein the bearing includes:
   a disk portion, which receives the linear force; and
   a radial flange, extending from the disk, which receives the radial braking force.

5. The system of claim 1, wherein the clamping assembly includes:
   an axle about which one of the first and the second housing members is rotatable; and
   a clamping means, associated with the axle, for locking the other of the first and the second housing members against rotation about the axle.

6. The system of claim 5, wherein the clamping means includes:
   a means for variably adjusting the linear clamping force.

7. The system of claim 6, wherein the means for variably adjusting includes a brake screw threadably connected with the axle.

8. The system of claim 1, wherein the spring arm mechanism includes:
   a rod;
   a spring received on the rod;

a force transferring member, received on the rod, an end of the spring applying a force to the force transferring member which is transferred by the force transferring member to the second housing member.

9. The system of claim 8, further including:

an axle about which the second housing member is rotatable;

a block, carried by the second housing member, which defines a bore for receiving the axle therethrough; and wherein the spring arm mechanism further includes: a linkage connected between the rod and the block.

10. The system of claim 8, further including an adjustment nut threadably mounted on the rod, and spaced from the by the force transferring member by the spring, adjustment of the adjustment nut varying the radial braking force on the bearing.

11. The system of claim 10, wherein the force applying member include an annular disk which is seated on an interior shelf of the arm.

12. The system of claim 9, wherein the linkage is pivotally connected with the block at a point radially outwardly spaced from the axle.

13. The system of claim 12, further including:

a pin defined by one of the first and second housing members; and a slot defined by the other of the housing members, in which the pin traverses, the pin and slot limiting a range of rotational positions of the second arm portion.

14. The system of claim 13, wherein as the pin moves between ends of the slot, the radial force varies.

15. The system of claim 14, wherein the radial force is greatest when the pin is at an end of the slot which positions the second arm portion at its maximum angle below horizontal when the first arm portion is in a vertical orientation above horizontal.

16. The system of claim 15, wherein the maximum angle below horizontal is about 85 degrees.

17. The system of claim 14, wherein the radial braking force is lowest when the pin is at an end of the slot which positions the second arm portion at its maximum angle above horizontal.

18. The system of claim 17, wherein the maximum angle above horizontal is about 15 degrees.

19. The system of claim 1, wherein the spring arm mechanism is carried by the second arm.

20. An arm assembly comprising:

first and second arm portions;

a joint for positioning the second arm portion in a range of rotational orientations relative to the first arm portion, the joint including:

a bearing, and first and second opposed housing members which apply a first braking force to the bearing; and a spring arm mechanism connected with the joint, and being at least partially received in the second arm portion, the spring arm applying a second braking force to the bearing in a direction generally perpendicular to the first braking force, the second braking force varying in relation to the rotational orientation of the second arm portion relative to the first arm portion.

21. The arm assembly of claim 20, wherein the second breaking force increases as a force generated by the spring arm mechanism, which tends to rotate the second arm portion in a generally upward direction, increases, thereby reducing the tendency of the second arm portion to drift.

22. A method of balancing an arm portion of an arm assembly, the arm assembly including a joint having first and second relatively rotatable housing members spaced by a bearing, the arm portion being connected to the second housing member, comprising:

applying a clamping pressure between the housing members and the bearing in a first direction to create a constant braking force which resists rotation of the second housing member relative to the first housing member;

applying a variable clamping pressure between at least one of the housing members and the bearing in a direction generally perpendicular to the first direction to provide a variable braking force which resists rotation of the second housing member relative to the first housing member, the variable clamping pressure varying according to the relative rotational positions of the first and second housing members.

* * * * *